United States Patent [19]

Bowman et al.

[11] Patent Number: 4,786,745
[45] Date of Patent: Nov. 22, 1988

[54] 2,2-DIHALOVINYL HALOFORMATES AND PROCESS OF PREPARATION

[75] Inventors: Mark P. Bowman; Roy A. Olofson, both of State College, Pa.; Thierry Malfroot, Saintry Sur Seine; Jean-Pierre Senet, Herbeauvilliers-Buthiers, both of France

[73] Assignee: Societe Nationale des Poudres et Explosifs, Paris, France

[21] Appl. No.: 896,605

[22] Filed: Aug. 13, 1986

[30] Foreign Application Priority Data

Aug. 23, 1985 [FR] France ................................ 85 12652

[51] Int. Cl.$^4$ ........................ C07C 68/02; C07C 69/96
[52] U.S. Cl. .................................... 558/283; 558/280; 558/282; 560/30; 560/161
[58] Field of Search ........................ 558/283, 280, 282; 560/229

[56] References Cited

U.S. PATENT DOCUMENTS

| | | | |
|---|---|---|---|
| 2,221,275 | 11/1940 | Taylor | 560/229 |
| 3,080,405 | 3/1963 | Larsen et al. | 560/229 X |
| 3,213,062 | 10/1965 | Ellingboe et al. | 558/283 X |
| 3,823,171 | 7/1974 | Pittman et al. | 560/229 X |
| 4,487,781 | 12/1984 | Morisawa et al. | 560/229 X |
| 4,592,874 | 6/1986 | Cagnon et al. | 558/283 |
| 4,606,865 | 8/1986 | Palmer et al. | 558/283 |

Primary Examiner—Werren B. Lone
Assistant Examiner—Vera C. Clarke
Attorney, Agent, or Firm—Bucknam and Archer

[57] ABSTRACT

Novel 2,2-dihalovinyl haloformates are described of general formula:

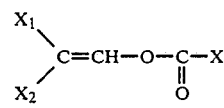

in which:
X is a chlorine or bromine atom;
$X_1$ and $X_2$ are the same or different and are chlorine or bromine.

The compounds are prepared by reaction of a 1,2,2,2-tetrahaloethyl haloformate of formula:

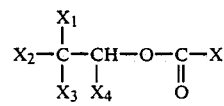

in which:
$X_1$, $X_2$ and X are as described hereinabove;
$X_3$ is chlorine or bromine and is always bromine when $X_1$ and/or $X_2$ is bromine and
$X_4$ is chlorine or bromine, with a metal such as zinc or magnesium in a solvent.

The novel compounds are very useful for the preparation of 2,2-dihalovinyl carbonates and carbamates which may be used as insecticides or as comonomers.

13 Claims, No Drawings

2,2-DIHALOVINYL HALOFORMATES AND PROCESS OF PREPARATION

The present invention relates to novel 2,2-dihalovinyl haloformates, their process of preparation and their applications.

A few unsaturated haloformates are known and described in the literature. For instance, U.S. Pat. No. 2,377,085 relates to vinyl chloroformates and 2-methyl-vinyl chloroformates. French No. 2,421,866 describes isopropenyl chloroformate.

Vinyl fluoroformate has been prepared by P. Beak and J. A. Barron, J. Org. Chem., 38 (16) pp. 2771–2775 (1973) and vinyl iodoformate has been described by H. M. R. Hoffmann and L. Iranshahi, J. Org. Chem., 49, pp. 1174–1176 (1984).

However, there is no mention in the literature with respect to dihalogenovinyl haloformates in spite of the fact that these substances are very useful in order to introduce the dihalovinyl group into another compound. Clearly, therefore, it is of great interest to prepare this type of compounds and to provide a method for their preparation.

The new halogenoformates according to the invention are represented by the formula hereinbelow:

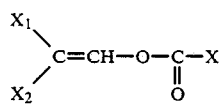

in which:
X is a chlorine or bromine atom;
$X_1$ and $X_2$ are the same or different and are chlorine or bromine.

In particular, the present invention relates to compounds in which X is an atom of chlorine and $X_1$ and $X_2$ are the same and are chlorine or bromine, that is 2,2-dichlorovinyl chloroformate of formula:

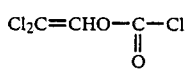

and 2,2-dibromovinyl chloroformate of formula:

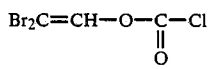

The invention relates also to the process of preparation of the novel halogeno formates. The process for the preparation of the novel compounds consists of reacting a 1,2,2,2-tetrahaloethyl haloformate of formula:

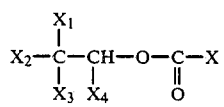

in which:
$X_1$, $X_2$ and X are as described hereinabove;
$X_3$ is chlorine or bromine and is always bromine when $X_1$ and /or $X_2$ is bromine; and
$X_4$ is chlorine or bromine with a metal such as zinc or magnesium in a solvent.

The reaction scheme is as follows:

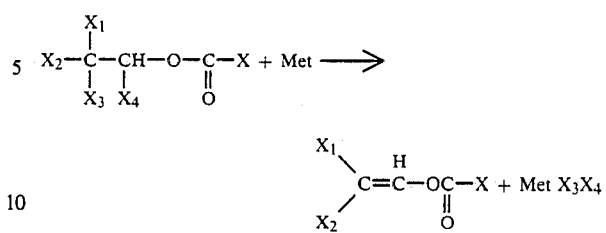

It is surprising that this reaction leads to the unsaturated dihalo haloformates because it is well known that metals such as zinc or Lewis acids such as, for instance, zinc chloride cause a decomposition of the chloroformates by decarboxylation (see M. Matzner et al, Chem. Review, 64, pp. 668 and 670 (1964)) as shown hereinbelow:

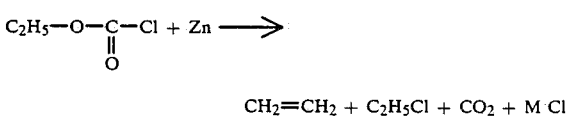

$$CH_2=CH_2 + C_2H_5Cl + CO_2 + M\ Cl$$

The 1,2,2,2-tetrahaloethyl haloformates starting material are easily prepared for instance by reaction of a trihaloacetaldehyde of formula:

withacarbonyl dihalide of formula:

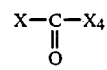

according to the method of preparation described in French Pat. No. 2,482,587.

According to a specific embodiment of the process, it is possible to replace the haloformate starting material with its constituents that is the trihaloacetaldehyde of formula:

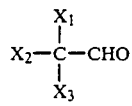

and the carbonyl dihalide of formula:

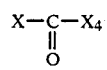

with $X_1$, $X_2$, $X_3$ and $X_4$ having the same meaning as described hereinabove.

The dehalogenation proceeds well with the haloformates such as 1,2,2,2-tetrachloroethyl chloroformate or 1-chloro-2,2,2-tribromoethyl chloroformate. As the metal, it is preferred to use powdered zinc rather than magnesium filings or in powder. Powdered zinc preferably is previously activated for instance according to the method described by Fieser and Fieser in "Reagents for Organic Synthesis", 1, pp. 1276, New York (1967) or it is possible to use copper colored powdered zinc prepared according to R. Wilkinson, J. Chem. Soc., pp. 3057 (1931). The amount of the metal is at least the stoichiometric amount and preferably in excess of 5-50%. The reaction takes place in a solvent or in a mixture of solvents preferably anhydrous. The solvents are selected among cyclic or open-chain ethers and esters by themselves or in mixture with the ethers. Tetrahydrofuran, dioxane, diethyl ether, dimethoxyethane, ethylacetate and methylacetate are suitable. The temperature usually is between 0° and 60° C. preferably between +5° and 30° C.

The reaction time in general is between 30 minutes and a few hours. The solvents are then eliminated, for instance by heating or under vacuo. The zinc salts may be allowed to precipitate if necessary. The product, the 2,2-dihalovinyl haloformate may be recovered by distillation.

The process according to the invention permits starting from readily available starting materials to obtain in a simple manner and with good yields, the haloformates which are particularly useful because they contain the vinyl function and in addition two halogen atoms attached to the vinyl group. In view of this group, they may be used as monomers to prepare new polymers or they may be used as intermediates in organic syntheses.

The invention relates also to the novel uses of the novel compounds.

According to one application, the 2,2-dihalovinyl haloformates are allowed to react with ammonia, a primary amine, a secondary amine, a compound containing hydroxyl groups such as a diol or an alcohol or a phenol to form carbamates or carbonates containing the 2,2-dihalovinyl group. The reactions are shown hereinbelow:

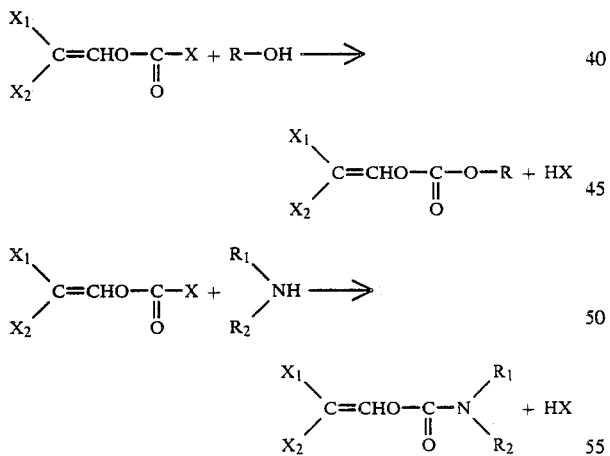

The reaction conditions are known, see for instance, Chemical Review, 64, pp. 651–657.

By means of the novel haloformates according to the present invention, carbamates and carbonates containing the 2,2-dihalovinyl group and particularly the 2,2-dichlorovinyl group are prepared. These carbamates and carbonates are obtained with a yield substantially superior to the complex procedure known in the art described in British Pat. No. 1,221,205. These substances are very useful to increase the efficacy of insecticides or they may be polymerized with other monomers for instance ethylene for the purpose of modifying the properties of other polymers as described in British Pat. No. 1,221,205.

The following examples illustrate the invention and are not intended to be limitative.

EXAMPLE 1

Preparation of 2,2-dichlorovinyl chloroformate from 1,2,2,2-tetrachloroethyl chloroformate

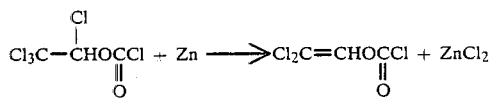

Powdered zinc (Aldrich) in the amount of 7.9 g (0.12 mole; 1.09 equivalent) is added in small portions by means of a powder distributor and under stirring to a solution of 27.3 g (0.11 mole) of 1,2,2,2-tetrachloroethyl chloroformate in 100 cc of tetrahydrofuran. In view of the initial induction phase a new portion of zinc powder is added only after the previous portion has been used up. After the addition of zinc, the reaction mixture is allowed to stand under stirring for four hours and then it is evaporated in a vacuum of 0.5 mm Hg and the volatile components are collected in a trap kept at −78° C. By fractional distillation under vacuo, there is obtained 15 g (75% yield) of the desired product.

b. p.: 82–85° C./120 mm Hg

I. R. ($CCl_4$) cm$^{-1}$: 3104 (average), 1785 (strong), 1131 (very strong)

$RMN^1H$ ($CDCl_3$) δppm: 7.50 (s)

$RMN^{13}C$ ($CDCl_3$) δppm: 147.3 (d, J=2.9 Hz, C=0) 134.1 (d, J=204.9 Hz, =CH—) 116.3 (d, J=11.8 Hz, $Cl_2C$=).

EXAMPLE 2

Preparation of 2,2-dichlorovinyl chloroformate by reaction of phosgene with chloral in the presence of zinc

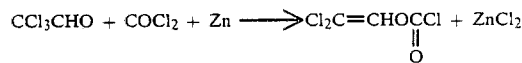

Liquid phosgene in the amount of 10 cc (0.14 mole; 1.5 equivalent) is introduced into a stirred suspension of 0.1 g zinc powder in a mixture of 30 cc of methyl acetate previously distilled over phosphorus pentoxide and 15 cc of ether previously dried over sodium.

After 15 minutes, chloral in the amount of 13.8 g (0.0938 mole) distilled in a column of anhydrous calcium sulfate according to Perrin, Armarego, Perrin in "Purification of Laboratory Chemicals" 2nd Ed., p. 162, Pergamon Press, London (1980), is added. After the first portion of the zinc powder has been used up, the remainder is added in portions, that is 8 g, (0.12 mole) by means of a teflon powder distributor. It is necessary to make sure that each portion of the zinc powder is used up prior to introducing the next portion. The reaction medium is kept at room temperature by means of a cold water bath.

The mixture is kept under stirring for two hours and then the excessive phosgene is removed under vacuo. The liquid residue is filtered by means of a fritted glass filter (25–50μ) and the orange filtrate is distilled in a vacuum of 1.5 mm Hg at room temperature into a trap kept at −80° C.

In order to extract the last amounts of the product from the distillation residue, 3 cc of nitrobenzene, distilled over phosphorous pentoxide, is added and then the vacuum distillation is continued. By fractional distillation of the liquid collected in the trap, (37°–40° C./15 mm Hg), there is obtained 2,2-dichlorovinyl chloroformate, 8.37 g (51% yield) with the same properties as described in Example 1.

EXAMPLE 3

Preparation of 2,2-dibromovinyl chloroformate starting from 1-chloro-2,2,2-tribromoethyl chloroformate

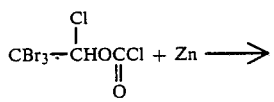

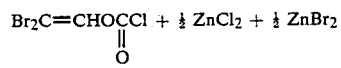

Powdered zinc, activated according to Fieser and Fieser, "Reagents for Organic Synthesis", 1, p. 1276, Wiley, New York (1967), in the amount of 1.1 g (0.017 mole; 1.3 equivalent) is added in small portions by means of a powder distributor in the course of about two hours and under stirring to a solution of 5.02 g (0.0132 mole) of 1-chloro-2,2,2-tribromoethyl chloroformate in 10 cc of ethylacetate previously distilled over phosphorous pentoxide. After stirring for 30 minutes, there is added 10 cc of a mixture 2/1 pentane/dioxane (pentane distilled over sodium benzophenone and dioxane distilled over lithum aluminum hydride) for the purpose of precipitating the zinc salts.

After filtration, the solution is concentrated under vacuo and again filtered. There is then added 5 cc of 1-chloronaphthalene and the solution is distilled at 35°–70° C. in a vacuo of 0.4 mm Hg into a trap kept at −78° C. The product is purified by fractional distillation thus giving 1.14 g (32% yield) of pure 2,2-dibromovinyl chloroformate.

b.p.: 68°–69° C./12 mm Hg
IR (CCl$_4$) cm$^{-1}$: 1 3090 (weak), 1782 (strong)
RMN$^1$H (CDCl$_3$) δppm: 7.75 (s)
RMN$^{13}$C (CDCl$_3$) δppm: 147.3 (d, J=2.7 Hz, C=O) 138.3 (d, J=204.3 Hz, =CH—) 84.2 (d, J=12.3 Hz, Br$_2$C=)

EXAMPLE 4

Preparation of 2,2-dichlorovinyl chloroformate by reaction of phosgene with chloral in the presence of magnesium Phosgene, in the amount of 5.2 g (0.053 mole; 1.8 equivalent) is added to a stirred mixture of 4.41 g of chloral (0.030 mole), 0.86 g (0.035 mole; 1.2 equivalent) of magnesium in powder form (Mallinckrodt, 40 mesh) and 25 cc of ethylacetate. After stirring for 40 minutes at the temperature of about 20° C., RMN$^1$H analysis with internal standard shows the formation of the desired 2,2-dichlorovinyl chloroformate with a 6% yield.

EXAMPLE 5

Use of 2,2-dichlorovinyl chloroformate in the preparation of 2,2-dichlorovinyl N-(3-chlorophenyl) carbamate

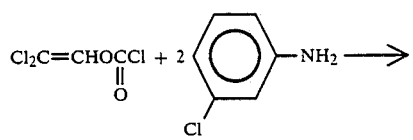

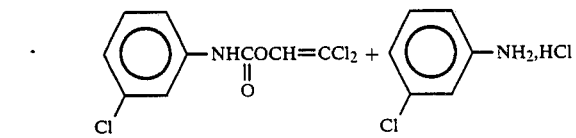

Into a 500 cc vessel are introduced 17.55 g (0.1 mole) of 2,2-dichlorovinyl chloroformate and 60 g of diethyl ether. The mixture is cooled to 0° C. and then there is added during the course of 30 minutes, under stirring, a solution of 25.5 g (0.2 mole) of 3-chloro aniline in 50 g of ether. The mixture is let stand under stirring for two hours at a temperature of about 20° C., it is then filtered, the filtrate is washed with water, dried over magnesium sulfate and the solvent is evaporated. The desired product, the carbamate, is obtained; 26.5 g (99% yield).
Purity>98%
m.p.: 94° (literature: 92°–93° C. according to Example 4 of British Pat. No. 1,221,205)

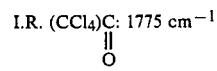

RMN$^1$H (CDCl$_3$) δppm: 7.1 (m, 4H) 7.35 (m, 1H) 7.45 (s, 1H)

EXAMPLE 6

Use of 2,2-dichlorovinyl chloroformate in the preparation of 2,2-dichlorovinyl phenyl carbonate

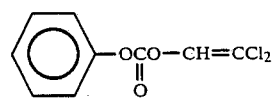

Into a 250 cc vessel are introduced 10.3 g (0.11 mole) of phenol, 19.3 g (0.11 mole) of 2,2-dichlorovinyl chloroformate and 150 g of chloroform. The mixture is cooled to 0° C. and then during the course of 30 minutes, there is added under stirring 11 g of a solution of 50% aqueous sodium hydroxide.

The mixture is allowed to stand at room temperature for one hour under stirring, it is then washed with water and the solvent is evaporated under reduced pressure. The desired carbonate is obtained; 21.3 g (83% yield), see Example 7 of British Pat. No. 1,221,205. The product has the appearance of a white solid of melting point<50° C.

IR (CCl$_4$) 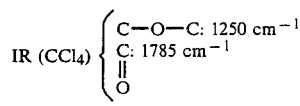

RMN$^1$H (CDCl$_3$) δppm: 7.3 (m, 5H) 7.45 (s, 1H)

EXAMPLE 7

Preparation of 2,2-dibromovinyl chloroformate by reacting phosgene with bromal in the presence of zinc Activated zinc dust (10 g, 0.15 mol, 0.5 equiv) was added in small portions over 5 days to a stirred solution of bromal (80.2 g, 0.29 mol) in 75 ml of 2:1 ethyl acetate/ether and phosgene (38 ml, 0.5 mol). After 7 days with some zinc dust remaining, the excess phosgene was removed and the mixture was filtered. Most of the zinc salts were removed by washing three times with a mixture of hexane (50 ml) and dioxane (30 ml). The solvents were removed by simple distillation and then by distillation at reduced pressure. The obtained product has been fractionally distilled to be purified and exhibited the same properties than the 2,2-dibromovinylchloroformate obtained in example 3:

IR (CCl$_4$) cm$^{-1}$: 3 090 (weak), 1 780 (strong)

RMN$^1$H (CDCl$_3$) δppm : 7.75.

What is claimed is:

1. A 2,2-dihalovinyl haloformate of formula:

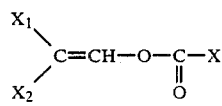

wherein:

X is chlorine or bromine;

X$_1$ and X$_2$ are the same or different and are chlorine or bromine.

2. A haloformate according to claim 1 wherein X$_1$, X$_2$ and X are chlorine.

3. A haloformate according to claim 1 wherein X$_1$ and X$_2$ are bromine and X is chlorine.

4. The process for the preparation of a haloformate according to claim 1, wherein 1,2,2,2-tetrahaloethyl haloformate of formula:

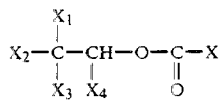

in which:

X$_1$, X$_2$ and X are as defined hereinabove;

X$_3$ is chlorine or bromine and is always bromine when X$_1$ and/or X$_2$ are bromine and X$_4$ is chlorine or bromine is reacted with zinc or magnesium in a solvent.

5. The process of preparation according to claim 4 wherein the solvent is anhydrous.

6. The process of preparation according to claim 4 wherein the reaction is carried out at a temperature between 0° and 60° C.

7. The process of preparation according to claim 6 wherein the temperature is between 5° and 30° C.

8. The process according to claim 4 wherein the metal is used in at least the stoichiometric amount.

9. The process according to claim 8 wherein the metal is used in excess of 5-50%.

10. The process according to claim 4 wherein activated powdered zinc or orange-colored powdered zinc is used.

11. The process according to claim 4 wherein the solvent is at least one member selected from the group consisting of open-chain ethers, cyclic ethers, and esters.

12. The process according to claim 11 wherein the solvent is a member selected from the group consisting of tetrahydrofuran, dioxane, diethyl ether, dimethoxyethane, ethylacetate and methylacetate.

13. The process according to claim 4 wherein said 1,2,2,2-tetrahaloethyl haloformate of formula:

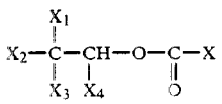

is prepared in situ by reaction of a trihaloacetaldehyde of formula:

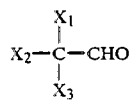

and a carbonyl dihalide of formula:

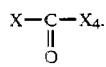

* * * * *